US 6,312,451 B1

(12) United States Patent
Streeter

(10) Patent No.: US 6,312,451 B1
(45) Date of Patent: *Nov. 6, 2001

(54) LOW LEVEL LASER THERAPY APPARATUS

(76) Inventor: Jackson Streeter, 3250 Marthiam Ave., Reno, NV (US) 89509

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/343,337

(22) Filed: Jun. 30, 1999

Related U.S. Application Data

(60) Provisional application No. 60/125,690, filed on Mar. 23, 1999, provisional application No. 60/125,691, filed on Mar. 23, 1999, provisional application No. 60/125,694, filed on Mar. 23, 1999, and provisional application No. 60/125,696, filed on Mar. 23, 1999.

(51) Int. Cl.[7] .................................................. A61N 5/00
(52) U.S. Cl. .................................. 607/89; 607/88; 606/3; 606/11
(58) Field of Search .................................. 607/88, 89, 92, 607/93; 606/2, 3, 10, 11, 9–12

(56) References Cited

U.S. PATENT DOCUMENTS

| 4,630,273 | * | 12/1986 | Inoue et al. ............................ 372/9 |
| 4,633,872 | * | 1/1987 | Chaffee et al. ........................ 606/11 |
| 4,669,466 | * | 6/1987 | L'Esperance ......................... 606/11 |
| 5,464,436 | * | 11/1995 | Smith .................................... 607/89 |
| 5,616,140 | * | 4/1997 | Prescott ................................ 606/10 |
| 5,755,752 | * | 5/1998 | Segal .................................... 607/89 |
| 5,879,376 | * | 3/1999 | Miller ................................... 607/89 |
| 6,146,410 | * | 11/2000 | Nagypal et al. ...................... 607/88 |

* cited by examiner

Primary Examiner—Michael Peffley
(74) Attorney, Agent, or Firm—Polster, Lieder, Woodruff & Lucchesi, L.C.

(57) ABSTRACT

Low level laser therapy apparatus for treatment of various tissue injuries is described. In one embodiment, the apparatus includes a handheld laser probe coupled to a control unit for selecting and controlling laser energy dosage from about 1 joule/point to about 10 joules/point. The apparatus emits laser energy at a wavelength from about 630 nm to about 904 nm, with a mean power output of between about 100 mW to about 500 mW. The apparatus further includes an access control mechanism to limit operability to trained personnel.

22 Claims, 3 Drawing Sheets

LOW LEVEL LASER THERAPY APPARATUS

CROSS-REFERENCE TO RELATED APPLICATIONS

This application claims the benefit of U.S. provisional applications Nos. 60/125,690; 60/125,691; 60/125,694; and 60/125,696, all of which were filed Mar. 23, 1999.

BACKGROUND OF THE INVENTION

This invention relates generally to laser apparatus and more particularly, to low level laser therapy apparatus.

High energy laser radiation is now well-accepted as a surgical tool for cutting, cauterizing and ablating biological tissue. High energy lasers are routinely used to vaporize superficial skin lesions, to make superficial incisions such as those required for plastic surgery, and to make deep cuts required for major surgical operations. Such lasers accomplish their results thermally, by heating the tissue.

Less well-known is that low levels of laser energy have a non-thermal, biostimulative effect on biological tissues. The therapeutic application of low level laser energy, frequently known as low level laser therapy (LLLT), produces beneficial clinical effects in the treatment of musculoskeletal, neurological and soft tissue conditions. LLLT is non-invasive and avoids the potential side effects of drug therapy. More specifically, LLLT delivers photons to targeted tissue, penetrating the layers of skin to reach internal tissues to produce a specific, nonthermal photochemical effect at the cellular level. Jeffrey R. Basford, Laser Therapy: Scientific Basis and Clinical Role, ORTHOPEDICS, May 1993, at 541.

Known LLLT devices and methods involve the application of laser energy at a wavelength in the near to mid infrared range, under certain limited conditions which limit the dosage of laser energy being applied. Known LLLT devices and methods involve the limited application of laser energy with devices having a very low average power output well below 100 mW. Such devices require extended periods of time to deliver any given dosage to a treatment point. Especially when multiple points are being treated, and multiple treatments required, longer treatment times are a significant inconvenience for both technician and patient. Some LLLT methods involve the application of laser energy to limited, specified sites for specific reasons. For example, known LLLT methods for treating specific pain symptoms involves applying laser energy to specific, charted treatment points which are correlated with the specific pain symptoms. However, such methods are limited to the treatment of specific symptoms, do not identify specific laser energy dosages, and do not provide any guidelines for varying dosages for treatment of a range of tissue injuries.

It would therefore be desirable to provide LLLT apparatus and methods for the treatment of a wide range of injuries. It would also be desirable to provide LLLT apparatus with which laser energy dosage can be varied. It would be further desirable to provide an LLLT apparatus which is capable of delivering laser light at a power output higher than about 100 mW, so that treatment times are reduced. It would be still further desirable to provide such LLLT apparatus with means to set dosage within a predetermined range. It would be yet still further desirable to provide such an LLLT device with an electronic locking mechanism which restricts accessibility to the device to authorized personnel.

BRIEF SUMMARY OF THE INVENTION

These and other objects may be attained by low level laser therapy apparatus which includes a handheld laser probe coupled to a control unit. In one embodiment, the probe includes a probe head in which are mounted four 30 mW GaAlAs laser diodes, emitting laser energy having a wavelength of 830 nm. The diodes are mounted in the probe head at an angle so that the laser beams emitted from the diodes substantially overlap or intersect at about 1.7 cm away from the head, producing a combined mean power output of 120 mW in the area of overlap.

In one embodiment, the control unit limits laser energy dosages to the range of about 1 joule/point, to about 10 joules/point, where a point is defined as a spot having a diameter of about 1 cm. The control unit is an AC powered box housing electronics for controlling the operation of the LLLT apparatus. The control unit includes an output display window for displaying a pre-selected laser energy dosage level in joules, associated electronics and a microprocessor storing in memory the preselected dosage level, and at least one dosage selection element such as a switch, knob or the like for pre-selecting the dosage level.

The control unit further includes a locking element for controlling access to, and use of, the LLLT apparatus. The locking element is, in one embodiment, a keyed lock configured to allow the LLLT apparatus to be operated only by individuals having a matching key.

DETAILED DESCRIPTION OF THE INVENTION

Figure 1:
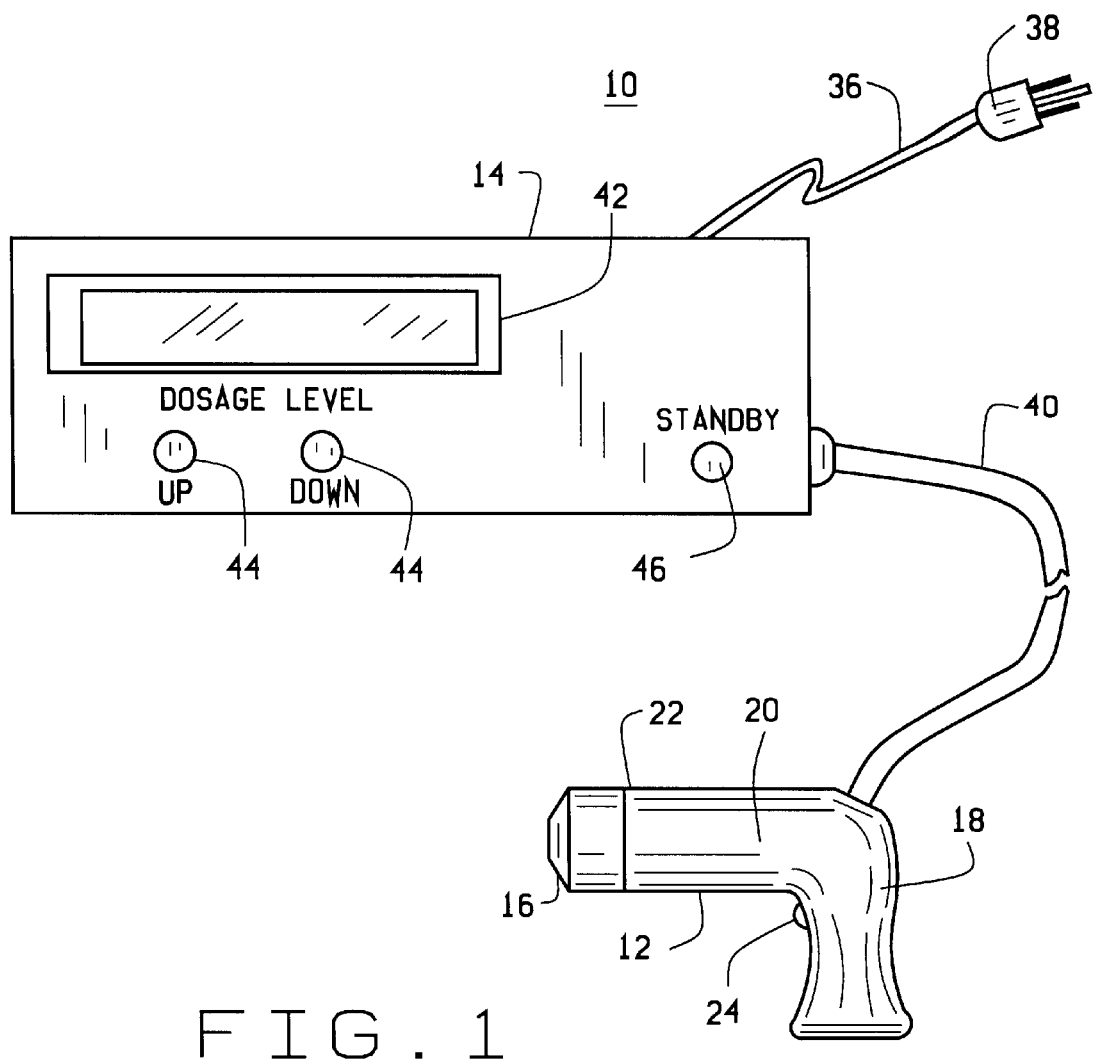
FIG. 1 is a schematic illustration of an LLLT apparatus.

FIG. 1 is a schematic illustration of an LLLT apparatus 10. LLLT apparatus 10 includes a handheld laser probe 12 coupled to a control unit 14. Probe 12 includes a probe head 16 in which laser diodes (not shown in FIG. 1) are mounted. In an exemplary embodiment, four 30 mW laser diodes are mounted in head 16 and angled so that laser beams emitted from the diodes intersect at a short distance away from the head, thus producing a combined mean power output of 120 mW at the point of intersection as described in more detail below. In one embodiment, probe 12 includes a handle portion 18 extending from barrel portion 20 in a substantially pistol-shaped configuration. Head 16 is at a distal end 22 of barrel portion 20. Handle portion 18 and barrel portion 20 are fabricated, for example, from a molded plastic material.

A switch button or trigger 24 is located on handle portion 18. The precise shape of probe 12 is varied among different ergonomic configurations to make repeated and prolonged use of probe 12 more comfortable. For example, in one embodiment handle portion 18 is molded with indentations forming a grip. In an alternative embodiment, probe 12 is a computer mouse-like element having a shape especially suitable for grasping from above, wherein the laser diodes are mounted on a bottom surface and button 24 is located in a position on the mouse-like element which is easily reached with, for example, the index finger. In another alternative embodiment, probe 12 has an elongate, penlight-like shape having two ends, with the laser diode or diodes mounted at one end and button 24 located in a position easily reached with an index finger when probe 12 is grasped as one would typically grasp a pencil.

To limit laser energy within a predetermined range, apparatus 10 includes control unit 14 which includes a box housing circuitry for controlling the operation of apparatus 10. An AC power cord 36 with a grounded plug 38 allows unit 14 to be plugged into a conventional electrical outlet. A second power cord 40 couples probe 12 to control unit 14. In an exemplary embodiment, unit 14 includes a display 42, such as an LED readout, for displaying a pre-selected laser energy dosage level in joules/point, a circuit board (not shown) including a control circuit, a microprocessor (not shown) linked to the control circuit and storing in memory the preselected dosage level, and at least one dosage selection element 44 such as a switch, knob or the like, linked to the control circuit for pre-selecting the dosage level. Generally, the control circuit functions to control the delivery of power to the laser diodes according to a predetermined dosage as selected using dosage selection element 44. In one embodiment as shown in FIG. 1, the dosage selection element 44 is a pair of buttons, with an "Up" button for increasing the dosage, and a "Down" button for decreasing the dosage. In an alternative embodiment, the dosage selection element is a single potentiometer, dial or the like for dialing in the preselected dosage. To limit laser energy dosages within a range, apparatus 10 includes control unit 14 which is a box generally housing circuitry for controlling the operation of apparatus 10. Referring again to FIG. 1, an AC power cord 36 with a grounded plug 38 allows unit 14 to be plugged into a conventional electrical outlet. A second power cord 40 couples probe 12 to control unit 14. In an exemplary embodiment, unit 14 includes a display 42, such as an LED readout, for displaying a pre-selected laser energy dosage level in joules; a circuit board (not shown) including a control circuit; a microprocessor (not shown) linked to the control circuit and storing in memory the preselected dosage level; and at least one dosage selection element 44 such as a switch, knob or the like, linked to the control circuit for pre-selecting the dosage level.

Generally, the control circuit functions to control the delivery of power to the laser diodes according to a predetermined dosage within a range, as selected using dosage selection element 44. In one embodiment as shown in FIG. 1, the dosage selection element 44 is a pair of buttons, with an "Up" button for increasing the dosage, and a "Down" button for decreasing the dosage. In an alternative embodiment, the dosage selection element is a single potentiometer, dial or the like for dialing in the preselected dosage. Of course, other implementations of the dosage control element will be obvious to those skilled in the electronics art. Control unit 14 further includes a locking element 46 for controlling access to, and use of apparatus 10. In an exemplary embodiment as shown in FIG. 1, control unit 14 includes a keyed lock 46 having an OFF position, a STANDBY position and an ON position. The STANDBY and ON positions can only be reached with a matching key (not shown). In the OFF position apparatus 10, including the diodes, is disabled. With the key, and with lock 46 in the STANDBY position, apparatus 10 is enabled for selecting the desired dosage using dosage control element 44. With lock 46 in the ON position and button or trigger 24 depressed, the laser diodes are energized for a period of time calculated by the memory chip to deliver the preselected dosage, the time being dependent on the total power output of the laser diodes.

Figure 2:
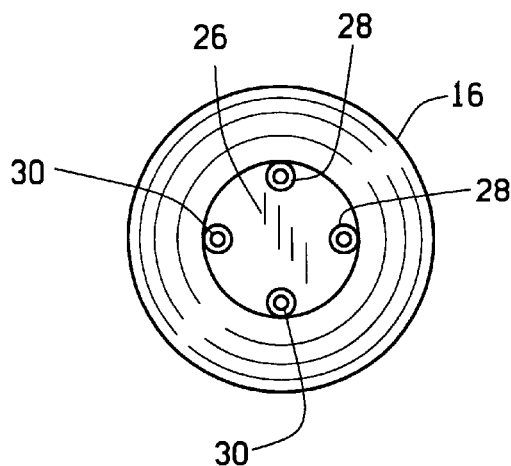
FIG. 2 is a plan view of the low level laser probe head.
Figure 3:
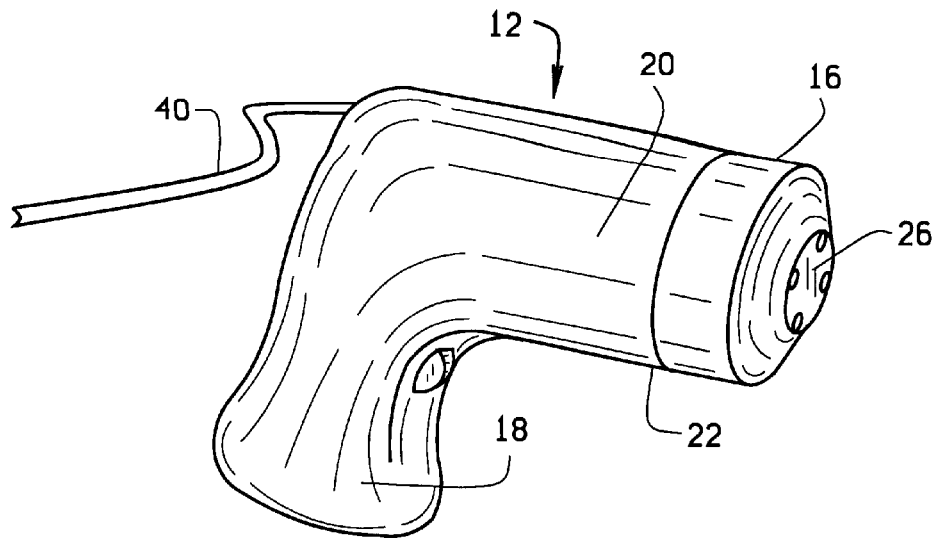
FIG. 3 is a perspective view of a low level laser probe.

FIG. 2 is a plan view of one embodiment of probe head 16. Probe head 16 is substantially cylindrical with a tapered forward end ending in a face 26 having openings 28 from which the laser energy is emitted. FIG. 3 is a perspective view of probe 12 showing more clearly the configuration of probe head 16. Probe head 16 is fabricated from, for example, a metal or plastic material and is coupled to barrel portion distal end 22. In an exemplary embodiment, four 30 mW laser diodes 30 are each mounted in an opening 28 in face 26, and angled so that laser energy beams emitted from each diode substantially overlap or intersect each other at a distance of about 0.5 to about 2.0 cm from face 26 to yield a combined power output of 120 mW in the overlapping area. In one embodiment, diodes 30 are angled in face 26 so that the laser energy beams overlap at a distance of about 1.7 cm from face 26. Generally, diodes 30 are any type which emits biostimulative laser energy, which includes lasers emitting energy at wavelengths between about 630 nm and about 904 nm.

The specific laser diodes chosen depends on the desired wavelength of the emitted laser energy, which depends on a number of factors including cost, as well as the desired level of penetration, and the type of tissue and injury being treated. In addition, some wavelengths appear to be especially suitable for specific applications. For example, low power HeNe lasers emitting at a relatively short wavelength of about 633 nm appear to be especially suited for conditions or injuries requiring lower levels of penetration, such as skin wounds, mucous membranes problems, and eye conditions such as conjunctivitis. However, for most internal tissue injuries amenable to LLLT, a penetration depth of about 2–3 cm is suitable, and is achieved with an intermediate wavelength of about 830 nm, that emitted by GaAlAs laser diodes. In addition to wavelength, the precise number and type of diodes used can be varied, limited only by the requirement that the combined or total mean power output be in the range of about 100 mW to about 500 mW, in pulsed or continuous mode.

Thus, in one embodiment diodes 30 are continuously emitting GaAlAs diodes emitting at a near-infrared wavelength of about 830 nm in a collimated beam. 30 mW GaAlAs diodes are relatively inexpensive, easily commercially obtained, and require only four to provide a mean power output in the range of about 100 mW to about 500 mW. However, higher or lower power GaAlAs diodes, or other biostimulative diodes emitting in the visible to near-infrared wavelength range of about 630 nm to about 904 nm may be used. For example, in one alternative embodiment, InGaAlP laser diodes are used, emitting at a wavelength of about 630–685 nm. In another alternative embodiment, pulsed GaAs diodes are used, emitting at about 904 nm. In other alternative embodiments, the combined or total power output is varied from about 100 mW to about 500 mW by changing the number and power of diodes used. For example, in one alternative embodiment, a single GAAlAs diode with a power output of 100 mW is used. As explained above, the precise number and type of diodes used is limited only by the requirement that the total power output be in the range of about 100 mW to about 500 mW. However, cost considerations are also a factor in deciding the number and types of diodes employed.

Figure 4:
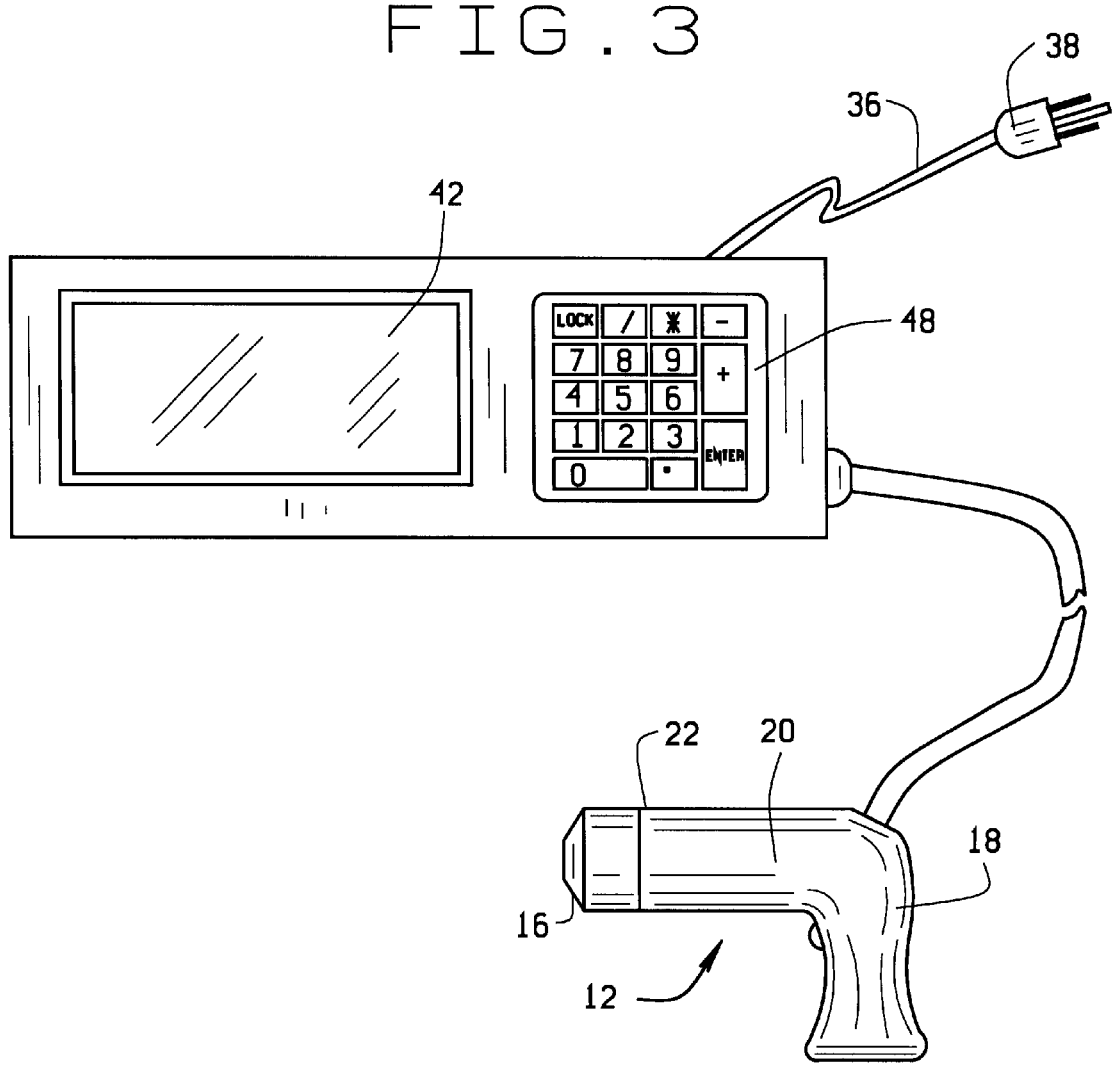
FIG. 4 is a schematic illustration of the LLLT apparatus with a PIN system.

FIG. 4 is a schematic illustration of an alternative embodiment of apparatus 10 in which locking element 46 is implemented with an access code system, such as a personal identification number (PIN) system. The PIN system includes a microprocessor (not shown) included in control unit 14. In this embodiment, control unit 14 includes display 42 and an input device 48 such as a keypad or LCD touch screen for entering data, including PIN's, into the microprocessor. In another alternative embodiment, control unit 14 is communicatively coupled to a compatible computer containing a microprocessor and having its own input device. The microprocessor stores hundreds or thousands of valid multiple-digit PIN's, each associated with a predetermined activation time. The predetermined activation time is a period of minutes sufficient to cover multiple treatments each lasting seconds or minutes. Upon entering a valid PIN, apparatus 10 is enabled to allow dosage selection, and then energizes diodes 30 when button or trigger 24 is depressed. In an alternative embodiment, instead of the PIN system as described above, control unit 14 includes a magnetic card reader for reading a card such as a credit card having a magnetically encoded authorization number for enabling apparatus 10.

As described above, each PIN is associated with a predetermined activation time. With each treatment or use lasting a limited period of seconds or minutes under a given PIN, the microprocessor is programmed to subtract the duration of use, or treatment time, from the activation time remaining on the given PIN. In one embodiment, the treatment time is calculated as the number of seconds or minutes during which diodes 30 are energized. Thus, microprocessor is programmed to keep account of the activation time remaining with each successive use of apparatus 10. For example, in one embodiment each PIN is associated with a total activation time of 100 minutes. With an average treatment time of 10 minutes per treatment, one PIN is used for a total of 10 treatments. Of course, the total number of minutes associated with a single PIN can be varied, as can the use of that time by the PIN holder. In one embodiment, the microprocessor is further programmed to issue a warning displayed on display 42 when a certain limited number of minutes remains in the activation time. For example, the microprocessor is programmed to issue a warning when 10 minutes remains of the total activation time on a given PIN. Of course, the time limit for issuing the warning can be varied.

In one embodiment, valid PIN's are provided via a computer network such as the Internet or Web so that a user of apparatus 10 can purchase activation time electronically. For example, a Web site on a server maintained by the manufacturer or seller of apparatus 10 is linked to a database which stores profile information on each user. A new user first registers with the Web site via a remote computer which is linked to the Web, providing profile information such as name, institution, billing information, and the like. When the profile information has been provided, or accessed from the database after being previously entered, and the user billed for the activation time, a valid PIN number for a predetermined activation time is provided to the user, for example by an automatic e-mail communication to the user, or through a separate Web page. The user then uses the PIN for LLLT treatment until the activation time is exhausted. If desired by the user, additional activation time is purchased in like manner and added, using a separate authorization code, to a previously used PIN so that the user does not need to repeatedly change his or her PIN. Of course, the electronic purchasing system is easily varied to use a magnetically encoded card as described above.

Figure 5:
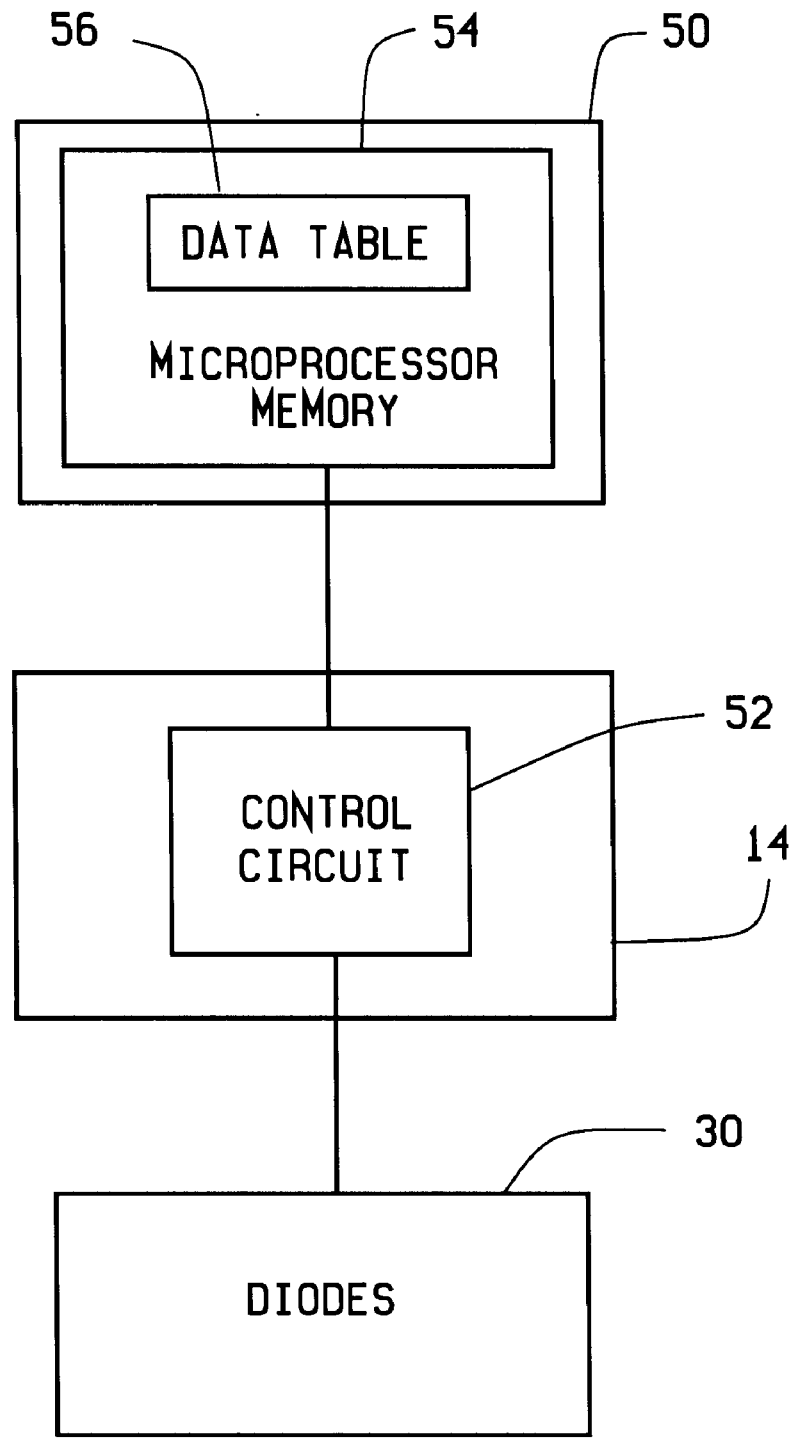
FIG. 5 is a block diagram of the LLLT apparatus.

FIG. 5 is a block diagram of apparatus 10, showing microprocessor 50 coupled to control circuit 52. In one embodiment, microprocessor 50 is programmed to store patient data information for individual patients, so that the user can easily monitor previous LLLT dosages and patient progress. For example, the microprocessor has an on-board memory 54 for storing patient information. In one embodiment, a data table 56 is stored in the microprocessor memory and includes an identifying code for each previous visit (for example the date), and the associated dosage(s), treatment times, codes for treatment locations, and other treatment information from previous treatments. In one embodiment, the patent data information includes a code for specifying the level and location of the patient's pain on each previous visit.

Apparatus 10 is used for treating a variety of tissue injuries, including musculoskeletal injuries, bone fractures, and spinal cord transections, and for improving local microcirculation, particularly cardiac microcirculation. Generally, a dosage of laser energy from about 1 joule/point to about 10 joules/point is chosen by a clinician based on the clinician's experience and training as well as the individual patient's previously demonstrated response to LLLT. The clinician, or a trained technician, accesses apparatus 10 with a key, PIN, or with a password for accessing a software control package as described above. The select dosage is dialed or otherwise input into control unit 14. With apparatus 10 enabled for the selected dosage, the clinician or technician applies face 26 of probe 12 to a point on the patient's skin surface over or near the internal tissue to be treated, applying enough pressure with face 26 at the skin surface so that the skin is slightly blanched. This step clears blood from the path of the laser energy to decrease absorption of the laser energy by the blood, thus allowing the greatest depth of penetration through the dermal structures to the internal injury. Button 24 is depressed and laser diodes 30 energized so that laser energy is applied, point by point, across the skin surface over the site or region of injury. If necessary, the treatment is repeated at intervals of about 1 to about 3 or 4 days. Number of treatment points and separation of treatment points, as well as the number of repeat treatments, varies with the location and type if injury, as well as the individual patient's response to LLLT.

More specifically, the LLLT apparatus is used to treat bone fractures as an adjunct therapy with established standard of care orthopedic treatments. To treat musculoskeletal injuries including repetitive strain injuries such as cervical strain and carpal tunnel syndrome, low level laser energy is applied to injured regions of muscle, tendon, ligament and fascial components. The LLLT apparatus is also used to improve local cardiac microcirculation, thus to prevent reperfusion injury to the myocardium after cardiac procedures such as bypass or angioplasty procedures. Specifically, the LLLT appartus is used to apply low level laser energy directly to the myocardium after surgery. The clinician applies adequate pressure with the probe so as to maintain contact with the myocardium. The LLLT apparatus is also used in combination with allogenic transplants for treating spinal cord transection. More specifically, embryonal nerve cells are cultured in vitro and then transplanted to a region of spinal cord transection. The in vitro cultured cells are placed in contact with both opposing surfaces or stumps of the transected spinal cord and form the basis for regenerated neural tissue which reconnects the transected surfaces. The transected area is then covered with a thin biocompatible membrane such as a fibrin-based membrane, and the site is closed in standard surgical fashion. The LLLT apparatus is used to deliver low level laser energy as described above to the transected area, starting immediately after surgery and continued daily to promote healing and neural regeneration, until the desired clinical results are achieved. As explained above, for all of these LLLT applications, the precise dosage chosen, treatment schedule and specific sites treated with LLLT varies according to the specific tissue injury and the patient's response. A trained clinician thus determines the treatment parameters for each patient.

Thus, the LLLT apparatus is used to treat a wide range of injuries and tissues. The LLLT apparatus delivers laser light in the biostimulative visible to near-infrared range within a dosage range, so that specific dosage is flexible. Further, the LLLT apparatus has a mean power output higher than about 100 mW, so that treatment times are shorter than those required by lower power devices. Still further, the LLLT apparatus includes an access control element which restricts accessibility to, and operability of the device to authorized, trained personnel. In addition, the lightweight, AC powered probe makes repeated applications of LLLT less fatiguing.

From the embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. Laser therapy apparatus comprising:
   a probe having an end face, said probe comprising a plurality of laser sources for emitting laser energy beams having a wavelength selected from the range of about 630 nm to about 904 nm, said probe configured so that the laser energy beams overlap at a distance of about 0.5 to about 2.0 cm from the probe end face, the laser sources each having a power output sufficient to produce a mean power output between about 100 mW and about 500 mW at the point of overlap; and
   a control element coupled to said probe, said control element configured to energize said plurality of laser sources for a variable period of time dependent on the selected wavelength of laser energy and the mean power output of the laser sources so that a pre-selected dosage of laser energy is emitted.

2. Apparatus in accordance with claim 1 wherein said pre-selected dosage of laser energy is from about 1 joule/point to about 10 joules/point.

3. Apparatus in accordance with claim 1 further wherein said control element comprises:
   a dosage selection element for selecting the pre-selected dosage; and
   a control circuit for automatically disabling said at least one laser source when the variable period of time has expired.

4. Apparatus in accordance with claim 1 wherein said plurality of laser sources comprises a GaAlAs laser diode.

5. Apparatus in accordance with claim 1 wherein the wavelength of said laser energy is about 830 nm.

6. Apparatus in accordance with claim 1 wherein said plurality of laser sources comprises from one to six laser diodes, each of said laser diodes having a mean power output between about 20 mW and about 100 mW and emitting the laser energy in a beam.

7. Apparatus in accordance with claim 6 wherein said probe comprises a probe head having a forward end, said laser diodes mounted at an angle in said probe head so that the laser energy beams substantially overlap at a distance from said forward end.

8. Apparatus in accordance with claim 1 wherein said mean power output of said laser sources is between about 120 mW and about 200 mW.

9. Apparatus in accordance with claim 1 wherein said mean power output of said laser sources is about 120 mW.

10. Apparatus in accordance with claim 1 wherein said mean power output of said laser sources is about 180 mW.

11. Apparatus in accordance with claim 1 wherein said control element further comprises a locking element for limiting operability of said apparatus to authorized personnel.

12. Apparatus in accordance with claim 11, said locking element comprising a keyed lock.

13. Apparatus in accordance with claim 11, said locking element comprising a microprocessor storing in memory a plurality of personal identification numbers (PIN's).

14. Apparatus in accordance with claim 13 wherein said microprocessor further stores in memory an activation time for each of said plurality of PIN's.

15. Apparatus in accordance with claim 13 further comprising an input device for entering data into said microprocessor.

16. Apparatus in accordance with claim 15 wherein said input device comprises an LCD touch screen.

17. Apparatus in accordance with claim 15 wherein said input device comprises a keyboard.

18. Apparatus in accordance with claim 15 further comprising a computer communicatively coupled to said control element, said computer providing said microprocessor and said input device.

19. A method of treating a body tissue, said method comprising the steps of:
   selecting a laser energy treatment wavelength from the range of about 630 nm to about 904 nm considering a desired level of tissue penetration, a type of injury and a type of tissue being treated;
   providing a low level laser therapy apparatus comprising a probe having an end face, said probe comprising a plurality of laser sources emitting laser energy beams having a wavelength selected from the range of about 630 nm to about 904 nm, said probe configured so that the laser energy beams overlap at a distance of about 0.5 to about 2.0 cm from the probe end face, the laser sources each having a power output sufficient to produce a mean power output between about 100 mW and about 500 mW at the point of overlap;
   pre-selecting a dosage of the laser energy at the selected wavelength;
   determining a treatment time, the treatment time being variable to obtain the pre-selected dosage of the laser energy;
   energizing the laser sources;
   applying the laser energy to the body tissue for the treatment time; and
   automatically disabling the laser sources after the variable treatment time has expired.

20. A method in accordance with claim 19 further comprising the step of applying the laser energy to at least one treatment point.

21. A method in accordance with claim 19 wherein pre-selecting a dosage of laser energy of the laser energy comprises selecting a dosage from about 1 joule/point to about 10 joules/point.

22. A method in accordance with claim 20 wherein applying the laser energy to at least one treatment point comprises the step of applying the laser energy to at least one treatment point located in an area of exposed skin adjacent the body tissue.

* * * * *